United States Patent [19]
McPhee

[11] Patent Number: 5,599,315
[45] Date of Patent: Feb. 4, 1997

[54] SYRINGE ACTUATION DEVICE

[75] Inventor: Charles J. McPhee, 8562 Larthorn Dr., Huntington Beach, Calif. 92646

[73] Assignee: Charles J. McPhee, Irvine, Calif.

[21] Appl. No.: 565,874

[22] Filed: Dec. 1, 1995

[51] Int. Cl.⁶ ................................... A61M 5/00
[52] U.S. Cl. .................... 604/218; 604/135; 604/246
[58] Field of Search .................. 604/218, 187, 604/132–137, 232, 263, 110, 131, 246

[56] References Cited

U.S. PATENT DOCUMENTS

| | | | |
|---|---|---|---|
| 2,472,116 | 6/1949 | Maynes | 128/218 |
| 2,565,081 | 8/1951 | Maynes | 128/218 |
| 2,591,457 | 4/1952 | Maynes | 128/218 |
| 3,880,163 | 4/1975 | Ritterskamp | 128/218 F |
| 3,882,863 | 5/1975 | Sarnoff et al. | 128/218 F |
| 4,316,463 | 2/1982 | Schmitz et al. | 128/218 F |
| 4,381,006 | 4/1983 | Genese | 128/218 A |
| 4,530,695 | 7/1985 | Phillips et al. | 604/184 |
| 4,597,754 | 7/1986 | Thill et al. | 604/154 |
| 4,623,330 | 11/1986 | Laby et al. | 604/63 |
| 4,755,172 | 7/1988 | Baldwin | 604/131 |
| 4,966,585 | 10/1990 | Gangemi | 604/133 |
| 4,997,420 | 3/1991 | LeFevre | 604/121 |
| 5,078,679 | 1/1992 | Reese | 604/51 |
| 5,100,389 | 3/1992 | Vaillancourt | 604/135 |
| 5,178,609 | 1/1993 | Ishikawa | 604/131 |
| 5,318,539 | 6/1994 | O'Neil | 604/118 |
| 5,320,609 | 7/1994 | Haber et al. | 604/135 |
| 5,330,430 | 7/1994 | Sullivan | 604/134 |
| 5,383,858 | 1/1995 | Reilly et al. | 604/152 |

FOREIGN PATENT DOCUMENTS 0584569  3/1994  European Pat. Off. .

Primary Examiner—John D. Yasko
Attorney, Agent, or Firm— Klein & Szekeres, LLP

[57] ABSTRACT

A syringe actuation device comprises an internally-threaded hollow outer sleeve with an open proximal end, and an externally-threaded hollow cylinder with a tapered internal diameter, that encloses a spring-biased piston, and that threads into the open distal end of the sleeve. The outer sleeve has a longitudinal opening parallel to its axis for receiving the fully-extended plunger of a pre-filled syringe, and a distal wall portion through which the barrel of the syringe extends. The cylinder contains a coil spring extending axially within its hollow interior, the spring having a proximal end seated against a proximal end wall of the cylinder, and a distal end attached to the proximal side of the piston. The piston is attached to the distal end of the spring so as to be pivotable from a canted orientation with respect to the cylinder's axis when the spring is compressed, to a substantially coaxial orientation with respect to the cylinder's axis when the spring is extended to a less compressed state. This pivoting function is facilitated by the tapered internal diameter of the cylinder, which decreases toward the distal end of the cylinder. This pivoting of the piston tends to equalize the axially-directed force component applied by the spring to the plunger as the spring decompresses, thereby substantially reducing the difference in flow rate from the syringe between the beginning and the end of the infusion process.

26 Claims, 2 Drawing Sheets

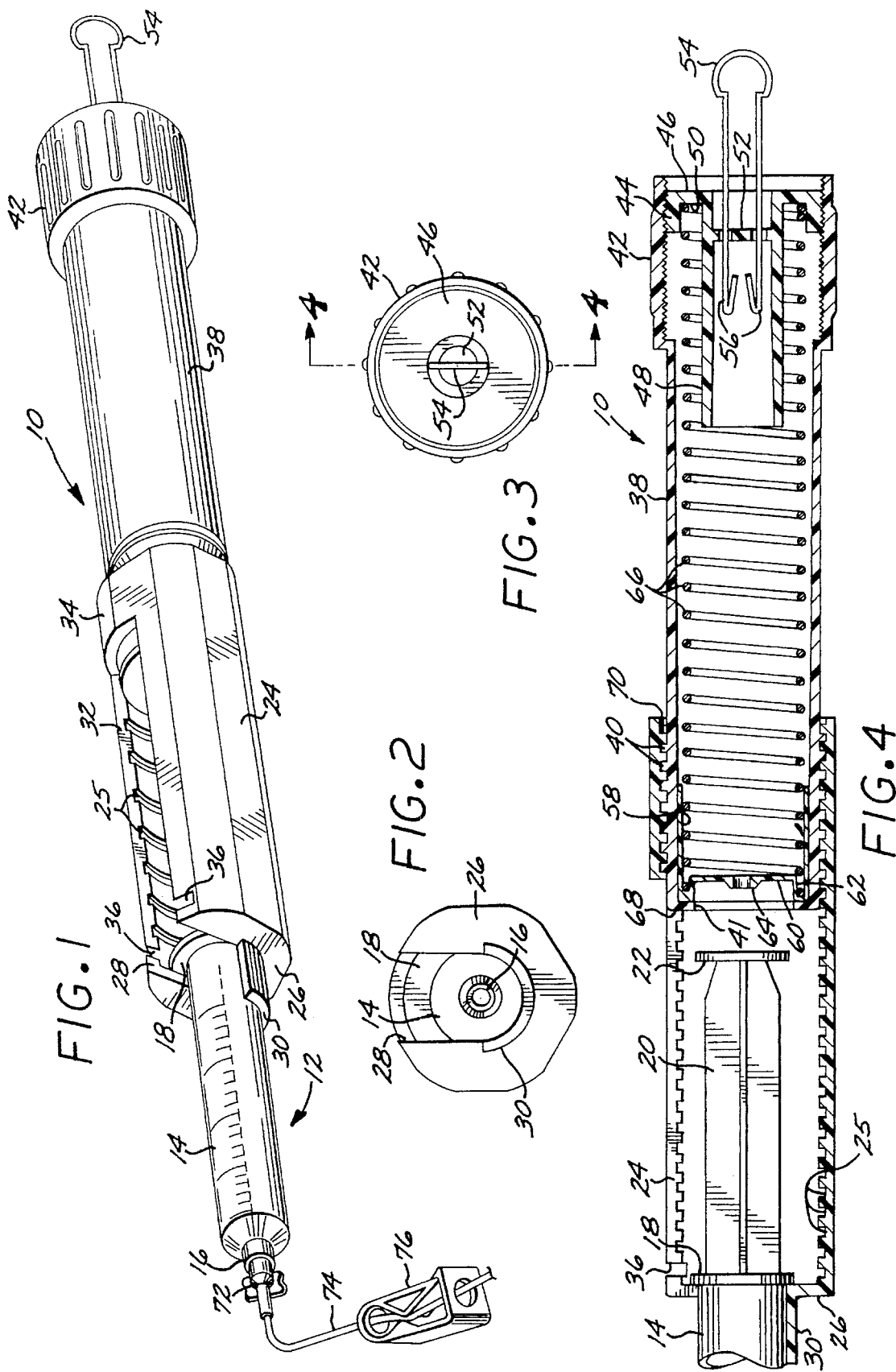

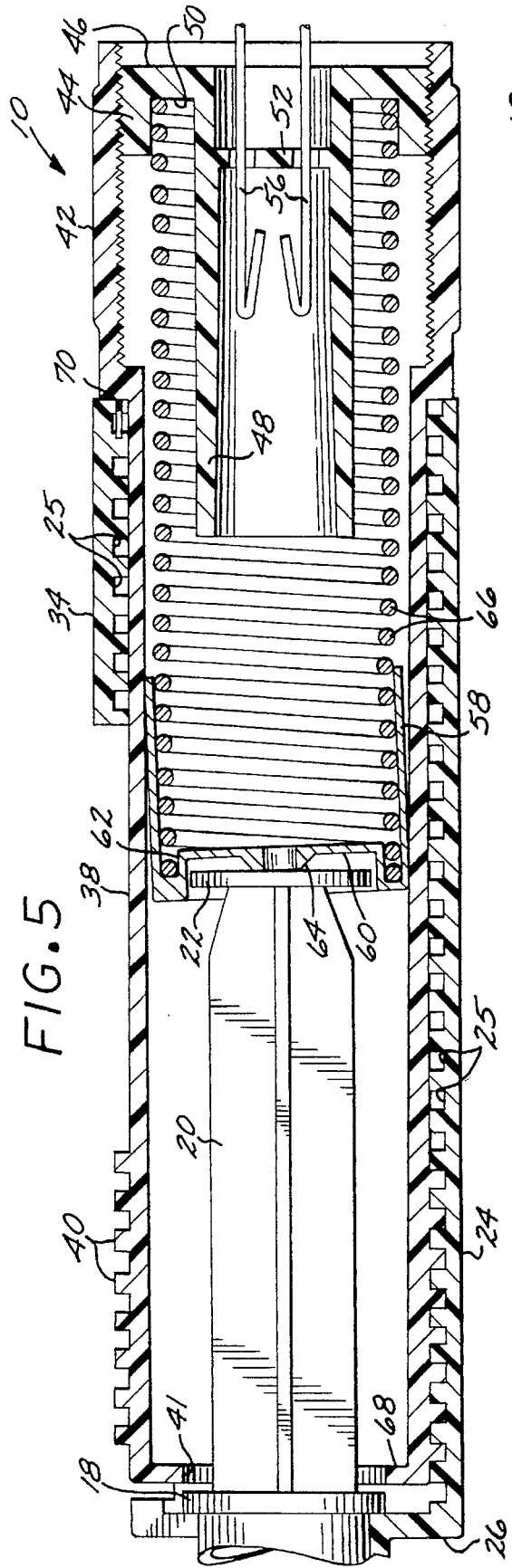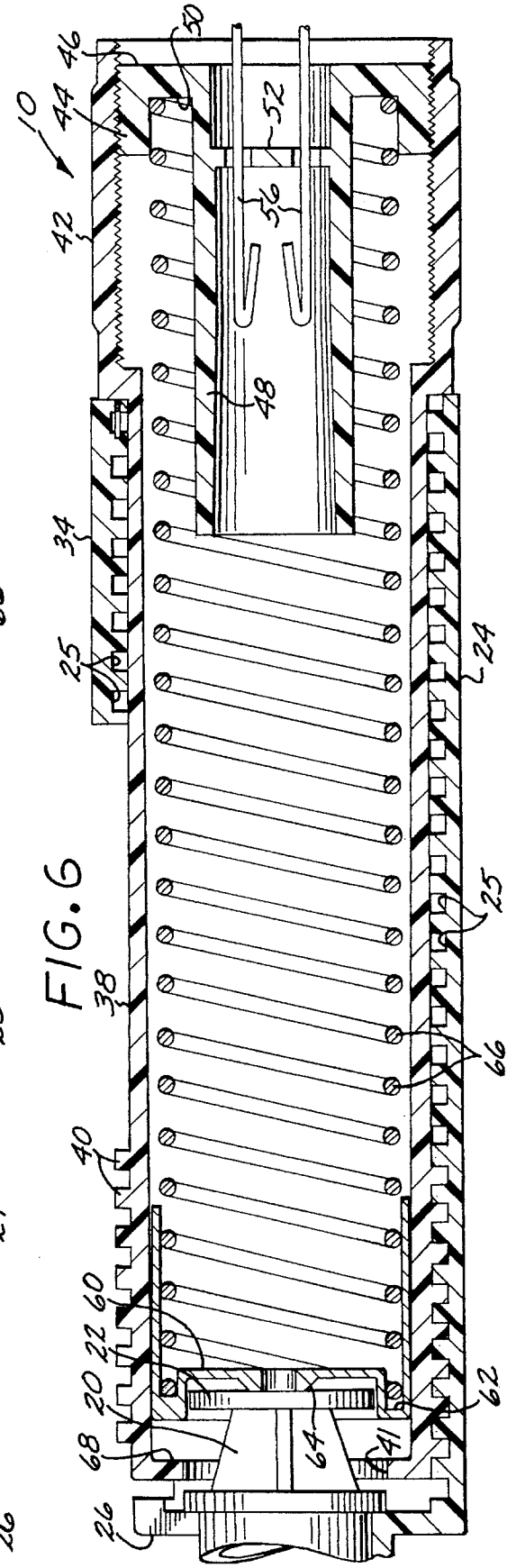

SYRINGE ACTUATION DEVICE

BACKGROUND OF THE INVENTION

This invention relates generally to the field of liquid infusion devices for medical applications. More specifically, it relates to mechanically-driven infusion devices used for the administration of a liquid medicament to a patient from a filled syringe into an intravenous (IV) administration system.

Various devices have been developed for the intravenous (IV) infusion of liquid medicaments into a patient at a controlled flow rate over an extended period of time. For example, gravity flow IV administration sets have been employed for many years, and more recently, IV administration sets with electrically powered pumps have been developed.

There are applications in which a more compact and inexpensive type of infusion device is desired or required. For example, in addition to direct infusion from a syringe, it is frequently necessary to infuse a secondary fluid into a primary IV flow from a gravity flow or electrically-pumped IV administration set. Also, infusion into an ambulatory patient frequently requires an infusion device that is less bulky, less complex, and easier to use than gravity flow or pump-powered devices. For such applications, relatively complex self-powered infusion devices are frequently used.

With a typical, manually actuated IV administration syringe, infusion over an extended period of time is usually impractical or inconvenient. Furthermore, even among syringes of the same size from the same manufacturer, the actuation forces required to provide a given fluid flow-versus-time profile vary greatly from syringe to syringe. Consequently, it is necessary to provide a sufficiently high actuation force to achieve a substantial degree of uniformity in fluid delivery from syringe to syringe. It has proven difficult consistently to achieve such sufficiently high syringe actuation forces with manually actuated syringes. To overcome these problems, the prior art has devised a variety of mechanisms for increasing the actuation force on the syringe throughout the infusion process. One type of syringe actuation mechanism is that which utilizes either internal or external springs to displace the plunger of the syringe. Examples of such mechanisms are shown in the following U.S. Patents: U.S. Pat. No. 2,472,116—Maynes; U.S. Pat. No. 2,565,081—Maynes; U.S. Pat. No. 2,591,457—Maynes; U.S. Pat. No. 3,880,163—Ritterskamp; U.S. Pat. No. 3,882,863—Sarnoff et al.; U.S. Pat. No. 4,381,006—Genese; U.S. Pat. No. 4,530,695 Phillips et al.; U.S. Pat. No. 4,597,754—Thill et al.; U.S. Pat. No. 4,623,330 Laby et al.; U.S. Pat. No. 4,755,172—Baldwin; U.S. Pat. No. 4,966,585—Gangemi; U.S. Pat. No. 4,997,420—LeFevre; U.S. Pat. No. 5,078,679—Reese; U.S. Pat. No. 5,100,389 Vaillancourt; U.S. Pat. No. 5,178,609—Ishikawa; U.S. Pat. No. 5,318,539—O'Neil; U.S. Pat. No. 5,320,609—Haber et al.; U.S. Pat. No. 5,330,430—Sullivan; and U.S. Pat. No. 5,383,858—Reilly et al. Another example is shown in European Patent Application Publication No. 584 569 A2.

The known prior art devices suffer from one or more shortcomings, however. For example, several of the above-listed patents show the use of "constant force" springs, which are elongated flat leaf springs coiled on a drum, to address this problem. Such springs, however, add expense, bulk, and mechanical complexity to the device.

Another drawback of some prior art devices is that they cannot be used with conventional syringes, and instead require the use of syringes that are specially-designed for use with the actuation device. Still another limitation of many prior art syringe actuation devices is that a relatively great physical effort is required to compress the plunger actuation spring, because these devices lack a sufficient mechanical advantage to reduce the "loading effort" any appreciable degree. Other syringe actuation devices of the prior art require the syringe to be disconnected from any downstream fluid conduits (such as an IV administration set) before being loaded into the actuation device. This limitation makes such devices disadvantageous for use in those clinical applications, such as IV administration procedures, in which it is advantageous to load a pre-filled syringe into the syringe actuation device while the syringe is connected to the IV conduit.

It would therefore be a significant advancement over the prior art to provide a syringe actuation device that overcomes the aforementioned limitations. Specifically, it would be advantageous to provide such a device that yields improved uniformity in syringe-to-syringe fluid flow rates without a mechanism of undue complexity, and which is usable with conventional syringes of varying sizes. Furthermore, it would be advantageous to provide such a syringe actuation device that also may be loaded without undue physical effort, and that may receive a pre-filled syringe while the syringe is connected to a downstream conduit.

SUMMARY OF THE INVENTION

Broadly, the present invention is a syringe actuation device for receiving and holding a pre-filled conventional syringe having a plunger that is axially movable into the syringe barrel for expressing the contents therefrom, the device comprising a spring-biased piston that is engageable against the plunger to drive the plunger into the syringe barrel under the force of the spring.

More specifically, the actuation device comprises an internally-threaded hollow outer sleeve with an open proximal end, and an externally-threaded hollow cylinder with a tapered internal diameter, that encloses a spring-biased piston, and that threads into the open distal end of the sleeve. The outer sleeve has a longitudinal opening parallel to its axis for receiving the fully-extended plunger of a pre-filled syringe, and a distal wall portion with an opening or slot through which the barrel of the syringe extends. The cylinder contains a coil spring extending axially within its hollow interior, the spring having a proximal end seated against a proximal end wall of the cylinder, and a distal end attached to the proximal side of the piston.

A significant point of novelty resides in the structure of the piston, and in its functional relationship with the tapered internal diameter of the cylinder. The piston is attached to the distal end of the spring so as to be pivotable from a canted orientation with respect to the cylinder's axis when the spring is compressed, to a coaxial orientation with respect to the cylinder's longitudinal axis when the spring is extended to a less compressed state. This pivoting function is facilitated by the tapered internal diameter of the cylinder, which decreases toward the distal end of the cylinder. This pivoting of the piston tends to equalize the axially-directed force component applied by the spring to the plunger as the spring decompresses, thereby substantially reducing the difference in flow rate from the syringe between the beginning and the end of the infusion process.

In use, the cylinder is backed out of the outer sleeve to its most proximal axial position, thereby allowing a pre-filled syringe to be installed in the outer sleeve through the longitudinal opening. The plunger of the pre-filled syringe is extended in the proximal direction to its withdrawn position, and the outlet tip of the syringe is connected to a fluid conduit (e.g., an IV line). Flow from the syringe is occluded by means of a line clamp or an in-line valve or the like. As the cylinder is threaded into the outer sleeve, the distal side of the piston bears against the thumb rest at the proximal end of the plunger. Because fluid flow out of the syringe is blocked, the plunger cannot be displaced axially into syringe barrel. Consequently, the continued threading of the cylinder into the outer sleeve causes the plunger to bear against the piston so as to displace the piston axially in the proximal direction, against the force of the spring, thereby compressing the spring.

When the conduit to which the syringe is connected is opened to permit fluid flow, the spring is permitted to decompress. The force of the spring as it decompresses pushes the piston axially in the distal direction against the plunger, thereby pushing the plunger axially into the barrel of the syringe to express the contents of the barrel out of the outlet tip of the syringe.

When the spring is at its fully compressed position, the total force it can apply to the plunger is substantially greater than the force applied to the plunger near the end of the distally-directed stroke of the piston. (Typically, for example, the spring force may decrease by twenty per cent or more from the beginning to the end of the distal stroke of the piston.) To compensate, at least in part, for this decrease in force, the piston is canted with respect to the axis of the cylinder when the spring is in its compressed state. This canting is facilitated by the internal diameter of the cylinder being measurably greater than the external diameter of the piston at the point along the length of the cylinder where the piston resides at the beginning of its distal stroke. Because of this canting of the piston, at the beginning of the piston's distally-directed stroke, when the total spring force is at its greatest, a part of the spring force is directed radially, rather than axially. Therefore, something less than the total spring force is applied to push the plunger into the syringe barrel.

As the piston is displaced distally by the decompression of the spring, the piston pivots gradually toward an orientation in which its plane is orthogonal to the axis of the cylinder, guided by the gradual reduction in the internal diameter of the cylinder. Thus, as the total spring force decreases as the spring decompresses, a larger proportion of the total spring force is directed axially against the plunger. Accordingly, the magnitude of the axially-directed component of the spring force remains nearly constant throughout a substantial portion of the distally-directed stroke of the piston, thereby resulting in a nearly constant fluid flow from the syringe throughout a substantial portion of the axial travel of the plunger.

From the foregoing, it can be seen that a syringe actuation device in accordance with the present invention provides sufficient syringe actuation force substantially to overcome non-uniformity in syringe-to-syringe operational characteristics, with a more nearly constant fluid flow rate as the syringe is emptied without the use of "constant force" springs and their attendant complexities. Furthermore, conventional syringes of various sizes can be used with the present invention, and these syringes can be installed in the actuation device of the present invention while they are connected to a fluid flow line. These and other advantages of the present invention will be more fully appreciated from the detailed description that follows.

BRIEF DESCRIPTION OF THE DRAWINGS

FIG. 1 is a perspective view of a syringe actuation device in accordance with a preferred embodiment of the present invention, showing the device with a pre-filled syringe installed therein, and showing the syringe connected to an IV line or the like;

FIG. 2 is an elevational view of the distal end of the syringe actuation device of FIG. 1, with a pre-filled syringe installed therein;

FIG. 3 is an elevational view of the proximal end of the syringe actuation device of FIG. 1;

FIG. 4 is a cross-sectional view taken along line 4—4 of FIG. 3, showing the syringe actuation device before the cylinder is threaded into the outer sleeve;

FIG. 5 is a cross-sectional view similar to that of FIG. 4, showing the spring of the syringe actuation device compressed by the syringe plunger after the cylinder has been threaded into the outer sleeve; and FIG. 6 is a cross-sectional view similar to that of FIG. 5, showing the syringe plunger axially displaced in the distal direction by the decompression of the spring.

DETAILED DESCRIPTION OF THE PREFERRED EMBODIMENT

Referring now to the drawings, a syringe actuation device 10, in accordance with a preferred embodiment of the invention, is shown with a conventional infusion syringe 12 installed therein for action.

The syringe 12 is of conventional design, comprising a hollow cylindrical chamber or barrel 14 communicating with an outlet tip 16 at its distal end. The proximal end of the barrel 14 terminates in an annular flange 18. A plunger 20 is disposed for axial movement within the barrel 14 between a proximal withdrawn position and a distal inserted position. The proximal end of the plunger 20 terminates in a flattened plate or thumb rest 22.

The actuation device 10 comprises a hollow outer sleeve 24 that has an internal thread 25 throughout its length. The sleeve 24 has an open proximal end and a distal end wall 26 interrupted by a vertical slot 28 that is dimensioned to receive the syringe barrel 14. Extending distally from the distal end wall 26 below the slot 28 is a semi-cylindrical support 30 upon which the syringe barrel 14 rests as it extends distally from the end wall 26. Extending proximally from the slot 28 is a longitudinal opening 32, parallel to the axis of the sleeve 24, that extends proximally along a substantial portion of the length of the sleeve 24, terminating at an annular collar portion 34 adjacent the proximal end of the sleeve 24. The width of the longitudinal opening 32 is greater than the width of the plunger 20, so that the plunger 20 may be installed in the sleeve 24 through the axial opening 32. A pair of arcuate slots 36 extend a short distance circumferentially from opposite sides of the longitudinal opening 32 near the distal end thereof. The arcuate slots 36 provide clearance for accommodating the flange 18 at the proximal end of the syringe barrel 14.

A hollow cylinder 38 has a distal portion with an external thread 40 that mates with the internal thread 25 of the sleeve 24, so that the distal end of the cylinder 38 can be threaded into the sleeve 24 through the open proximal end of the latter. The distal end of the cylinder 38 has a central aperture 41 dimensioned to allow the passage therethrough of the syringe plunger 20, as will be explained below. The internal diameter of the cylinder 38 decreases gradually from its proximal end to its distal end, for reasons that will be explained below.

The cylinder 38 may advantageously be provided with an increased-diameter gripping portion 42 adjacent its proximal end. The interior of the gripping portion 42 may advantageously be internally threaded to mate with an externally-threaded peripheral collar 44 of a closure member 46 that closes the proximal end of the second sleeve 38. The closure member 46 includes a hollow tubular sheath portion 48 that extends distally into the interior of the cylinder 38. Between the collar 44 and the sheath portion 48, the interior surface of the closure member 46 defines an annular surface that functions as a fixed spring seat 50, as will be described below. The interior of the sheath portion is closed near its proximal end by an end wall 52. A retractable wire hanger 54 has a pair of distally-extending legs 56 that pass through a pair of diametrically-opposed apertures in the end wall 52 and into the interior of the sheath portion 48. The hanger 54 may thus be selectively withdrawn from the sheath portion 48 when it is needed, and pushed into the sheath portion 48 when it is not needed.

An axially-movable piston 58 is disposed within the cylinder 38 adjacent the distal end thereof. The piston 58 comprises a hollow cylindrical member with an external diameter that is slightly less than the minimum internal diameter of the cylinder 38. The proximal end of the piston 58 is open, and the distal end of the piston 58 is closed by a circular pressure plate 60, the proximal surface of which is formed with a peripheral annular groove 62. The groove 62 has a maximum depth at one circumferential position, and it progressively decreases in depth toward the diametrically opposite circumferential position. The groove 62, with its varying depth, provides a movable spring seat that tends to equalize the force applied to the piston throughout its travel, as will be explained below. The distal surface of the pressure plate 60 is recessed to form a seat for the thumb rest 22 of the syringe plunger 20. A central protuberance 64, the purpose of which will be explained below, extends distally from the center of the pressure plate distal surface.

Disposed longitudinally in the cylinder 38 so as to be concentric with the sheath portion 48 is a coil spring 66 having a proximal end that seats against the fixed spring seat 50 defined by the closure member 46, and a distal end that seats in the groove 62 in the pressure plate 60 of the piston 58. The spring 66 has a compressed position (FIG. 5) and an extended position (FIG. 6), but it is under some compression even in its extended position. The spring 66, being substantially coaxial with the cylinder 38, thus applies an axially-directed force to the piston 58 so as to urge the piston 58 distally, the distal travel of the piston 58 being limited by an annular lip 68 directed radially inwardly around the central aperture 41 at the distal end of the cylinder 38.

The outer sleeve 24 and the cylinder 38 may advantageously be pre-assembled, so that the latter is pre-threaded part of the way into the former. With such an arrangement, it may be desired to make these two components inseparable, whereby the cylinder 38 is incapable of being backed all the way out of the sleeve 24. To this end, the most proximal turn of the internal thread 25 of the sleeve 24 may be obstructed with a longitudinally-disposed pin 70 or equivalent obstructing element.

The operation of the actuation device 10 may now be readily understood. The outlet tip 16 of a pre-filled syringe 12 is connected, by a conventional connector fitting 72, to a flexible conduit 74, such as an IV line. Once the syringe 12 is filled, outflow of liquid from it is blocked by a clamp 76, of conventional design, applied to the conduit 74 downstream from the outlet tip 16. With the barrel 14 of the syringe 12 filled, the plunger 20 is extended to its proximal withdrawn position, and, since flow from the syringe 12 is occluded, the plunger 20 cannot be moved to its distal inserted position.

With the cylinder 38 of the actuation device 10 at its most proximal position with respect to the sleeve 24, i.e., threaded into the outer sleeve 24 only about as far as the collar portion 34 of the latter, the longitudinal opening 32 of the sleeve 24 provides access for the plunger 20 of the syringe 12 to be received within the interior of the sleeve 24, with the syringe barrel 14 being received in the vertical slot 28 in the distal end wall 26 of the sleeve 24, as best shown in FIG. 1. When the syringe 12 is so situated, the flange 18 at the proximal end of the syringe barrel 14 is cleared through the arcuate slots 36 near the distal end of the longitudinal opening 32, so that the flange 18 seats against the interior (proximal) surface of the distal end wall 26, as shown in FIGS. 4 through 6.

The initial proximal position of the cylinder 38 with respect to the syringe 12 installed within the sleeve 24 is shown in FIG. 4. The spring 66 is in its most decompressed or extended position, whereby the piston 58 is urged to its most distal position in abutment against the lip 68 at the distal end of the cylinder 38. There is, as yet, no contact between the pressure plate 60 of the piston 58 and the thumb rest 22 of the plunger 20.

As the cylinder 38 is threaded distally into the sleeve 24, the protuberance 64 of the piston pressure plate 60 begins to bear against the plunger thumb rest 22. Since the plunger 20 is restrained from movement in the distal direction, as described above, and since the syringe 12 as a whole is restrained from movement in the distal direction by the abutment of the barrel flange 18 against the distal end wall 26 of the sleeve 24, the engagement of the pressure plate protuberance 64 against the thumb rest 22 causes the spring 66 to be compressed. Maximum compression is reached when the cylinder 38 is threaded into the sleeve 24 to its most distal position, i.e., when the gripping portion 42 of the cylinder 38 abuts against the collar portion 34 of the sleeve 34, as shown in FIG. 5. When the spring 66 is thus compressed, the piston 58 is canted or tilted with respect to the longitudinal axis of the cylinder 38, as shown in FIG. 5, as a result of the varying depth of the spring-seating groove 62 in the pressure plate and the tapered internal diameter of the cylinder 38, as mentioned above. Because the protuberance 64 has a relatively small surface area bearing against the thumb rest 22, frictional forces between the piston 58 and the thumb rest 22 are substantially reduced, thereby providing easier threading of the cylinder 38 into the sleeve 24, and reducing the rotational torque applied to the plunger 20 by the threading process.

When infusion is to begin, the clamp 76 is released, thereby allowing the outflow of the fluid contents of the syringe barrel 14 through the outlet tip 16 and the conduit 74. With fluid flow now unblocked, the plunger 20 may now be moved distally into the barrel 14 to express the fluid contents therefrom. Such movement of the plunger 20 is effected by the decompression of the spring 66, the force of which urges the piston 58 distally against the thumb rest 22 of the plunger 20, thereby forcing the plunger 20 to move distally into the syringe barrel 14 to express the contents of the syringe 12 out of the outlet tip 16.

As the piston 58 is moved distally by the spring 66, the engagement between the piston 58 and the tapered internal wall surface of the cylinder 38 causes the piston 58 to pivot so as to reduce the amount of its canting with respect to the longitudinal axis of the cylinder 38. In other words, as the piston 58 is displaced distally by the decompression of the spring 66, the piston 58 pivots gradually toward an orientation in which its axis is substantially coaxial with the longitudinal axis of the cylinder 38, as shown in FIG. 6. This pivoting action is facilitated by the protuberance 64 on the distal surface of the pressure plate 60.

The purpose of the pivoting action of the piston 58 is as follows: When the spring 66 is in its compressed the state (FIG. 5), the axis of the piston 58 is canted with respect to the axis of the cylinder 38. Thus, at the beginning of the piston's distally-directed stroke, when the total spring force is at its greatest, a part of the spring force is directed radially, rather than axially. Therefore, something less than the total spring force is applied to push the plunger 20 into the syringe barrel 14. As the piston 58 is displaced distally by the decompression of the spring 66, the piston 58 pivots gradually toward the orientation in which its axis is substantially coaxial with the axis of the cylinder 38. Thus, as the total spring force decreases as the spring 66 decompresses, a larger proportion of the total spring force is directed axially against the plunger 20. Accordingly, the magnitude of the axially-directed component of the spring force remains nearly constant throughout a substantial portion of the distally-directed stroke of the piston 58, thereby resulting in a nearly constant fluid flow rate from the syringe 12 throughout a substantial portion of the axial travel of the plunger 20.

When the syringe 12 is empty, the cylinder 38 is backed out of the sleeve 24 a short distance to separate the piston pressure plate 60 from the thumb rest 22, so that the syringe can simply be removed from the actuation device 10.

It will be appreciated from the foregoing description that the actuation device in accordance with the present invention can be employed with conventional syringes of a variety of sizes, yielding nearly constant fluid flow from such syringes throughout a substantial portion of the distal stroke of the plunger. Moreover, sufficient force is generated for satisfactory actuation of even relatively large capacity syringes, i.e., up to about 60 cc or more, with a high degree of uniformity in fluid flow characteristics among syringes of equal sizes and similar types. Furthermore, the syringe can readily be installed in the device even while the syringe is connected to an IV line or the like. Finally, these advantages are achieved with a mechanism that is relatively simple and inexpensive to manufacture and easy to operate.

While a preferred embodiment of the invention has been described herein, it will be appreciated that a number of variations and modifications will suggest themselves to those skilled in the pertinent arts. Such variations and modifications may be considered within the spirit and scope of the present invention, as defined in the claims that follow.

What is claimed is:

1. A device for actuating a syringe, wherein the syringe includes a barrel and a plunger movable axially within the barrel from a withdrawn position to an inserted position, the device comprising:

a hollow sleeve having an open proximal end, a distal end opening for receiving the syringe barrel therethrough, and a longitudinal opening extending from the distal end opening toward the proximal end and dimensioned to receive the syringe plunger in its withdrawn position;

a hollow cylinder having a proximal end and an open distal end dimensioned to be received in the proximal end of the sleeve, whereby the cylinder is axially movable within the sleeve between a proximal position and a distal position, the cylinder having an internal diameter that gradually decreases from the proximal end thereof to the distal end thereof;

a piston disposed for longitudinal movement within the cylinder between a proximal position and a distal position, the piston including a portion disposed so as to bear against the plunger when the plunger is disposed in the sleeve and the cylinder is at its distal position; and a spring-biasing element disposed within the cylinder and engaged with the piston so as to bias the piston toward its distal position;

whereby the piston is canted with respect to the longitudinal axis of the cylinder when the piston is in its proximal position, and wherein the piston is oriented substantially coaxially with the cylinder when the piston is in its distal position.

2. The device of claim 1, wherein the sleeve has an internal thread and the cylinder has an external thread that engages the internal thread, whereby the cylinder is threadable within the sleeve between its proximal position and its distal position.

3. The device of claim 1, wherein the cylinder has a proximal end defining a fixed spring seat, and wherein the spring-biasing element comprises a coil spring disposed longitudinally within the cylinder, and having a distal end seated against the piston and a proximal end seated against the fixed spring seat.

4. The device of claim 1, wherein the piston comprises a hollow, substantially cylindrical portion having an open proximal end, a closed distal end disposed so as to bear against the plunger when the plunger is disposed in the sleeve and the cylinder is at its distal position, and an outside diameter that is slightly less than the minimum inside diameter of the cylinder.

5. The device of claim 4, wherein the closed distal end of the piston includes a proximal surface that defines a movable spring seat, wherein the cylinder has a proximal end defining a fixed spring seat, and wherein the spring-biasing element comprises a coil spring disposed longitudinally within the cylinder, and having a distal end seated against the movable spring seat and a proximal end seated against the fixed spring seat.

6. The device of claim 5, wherein the movable spring seat includes an annular groove having a first circumferential position with a maximum depth, the groove progressively decreasing in depth toward a second circumferential position, diametrically opposite the first circumferential position, with a minimum depth.

7. The device of claim 4, wherein the closed distal end of the piston includes a distal surface having a distally-extending central protuberance disposed so as to be seatable against the plunger when the plunger is disposed in the sleeve and the cylinder is at its distal position.

8. A device for applying an axially-directed actuation force to a syringe plunger, of the type including a force-applying mechanism engageable against the plunger to apply the actuation force thereto, characterized by the force-applying mechanism having a first position at which the magnitude of the total force applied to the plunger is at a maximum value but the axially-directed actuation force is less than the total force applied to the plunger, and a second position at which the magnitude of the total force applied to the plunger is less than its maximum value and the axially-directed actuation force is approximately equal to the total force applied to the plunger.

9. The device of claim 8, wherein the force-applying mechanism comprises:

a hollow cylinder having a proximal end and a distal end with an opening dimensioned to receive the plunger;

a piston disposed for longitudinal movement within the cylinder between a proximal position and a distal position, the piston including a portion disposed so as to bear against the plunger when the plunger is received in the cylinder through the distal end opening thereof;

a spring disposed within the cylinder and engaged with the piston so as to bias the piston toward its distal position, the spring being in a compressed state when the piston is at its proximal position, and in an extended state when the piston is at its distal position; and pivoting means, operative on the piston, for canting the piston with respect to the longitudinal axis when the piston is in its proximal position, and for causing the piston to pivot as it moves from its proximal position to its distal position under the force of the spring, until the piston is oriented substantially coaxially with the cylinder when the piston is at its distal position.

10. The device of claim 9, wherein the pivoting means comprises an inside diameter of the cylinder that gradually decreases from the proximal end of the cylinder to the distal end thereof.

11. The device of claim 10, wherein the piston comprises a hollow, substantially cylindrical portion having an open proximal end, a closed distal end disposed so as to bear against the plunger when the plunger is received in the cylinder through the distal end opening thereof, and an outside diameter that is slightly less than the minimum inside diameter of the cylinder.

12. The device of claim 11, wherein the distal end of the piston includes a proximal surface with an annular groove in which the spring is seated, the groove having a first circumferential position with a maximum depth, the groove progressively decreasing in depth toward a second circumferential position, diametrically opposite the first circumferential position, with a minimum depth.

13. The device of claim 11, wherein the closed distal end of the piston includes a distal surface having a distally-extending central protuberance disposed so as to be seatable against the plunger when the plunger is disposed in the cylinder through the distal end opening thereof.

14. An infusion system, comprising:

a hollow sleeve having an open proximal end, a distal end opening, and a longitudinal opening extending from the distal end opening toward the proximal end;

a syringe, including a barrel and a plunger movable axially within the barrel from a withdrawn position to an inserted position, the syringe disposed in the sleeve so that the barrel extends distally through the distal end opening and the plunger extends longitudinally within the sleeve toward the proximal end thereof;

a hollow cylinder having a proximal end and an open distal end dimensioned to be received in the proximal end of the sleeve, whereby the cylinder is axially movable within the sleeve between a proximal position and a distal position, the cylinder having an internal diameter that gradually decreases from the proximal end thereof to the distal end thereof;

a piston disposed within the cylinder so as to bear against the plunger when the cylinder is at its distal position, and movable longitudinally within the cylinder between a proximal position and a distal position; and a spring-biasing element disposed within the cylinder and engaged with the piston so as to bias the piston toward its distal position, thereby to urge the plunger from its withdrawn position to its inserted position;

whereby the piston is canted with respect to the longitudinal axis of the cylinder when the piston is in its proximal position, and wherein the piston is oriented substantially coaxially with the cylinder when the piston is in its distal position.

15. The system of claim 14, wherein the sleeve has an internal thread and the cylinder has an external thread that engages the internal thread, whereby the cylinder is threadable within the sleeve between its proximal position and its distal position.

16. The system of claim 14, wherein the cylinder has a proximal end defining a fixed spring seat, and wherein the spring-biasing element comprises a coil spring disposed longitudinally within the cylinder, and having a distal end seated against the piston and a proximal end seated against the fixed spring seat.

17. The system of claim 14, wherein the piston comprises a hollow, substantially cylindrical portion having an open proximal end, a closed distal end disposed so as to bear against the plunger when the cylinder is at its distal position, and an outside diameter that is slightly less than the minimum inside diameter of the cylinder.

18. The system of claim 17, wherein the closed distal end of the piston includes a proximal surface that defines a movable spring seat, wherein the cylinder has a proximal end defining a fixed spring seat, and wherein the spring-biasing element comprises a coil spring disposed longitudinally within the cylinder, and having a distal end seated against the movable spring seat and a proximal end seated against the fixed spring seat.

19. The system of claim 18, wherein the movable spring seat includes an annular groove having a first circumferential position with a maximum depth, the groove progressively decreasing in depth toward a second circumferential position, diametrically opposite the first circumferential position, with a minimum depth.

20. The system of claim 17, wherein the closed distal end of the piston includes a distal surface having a distally-extending central protuberance disposed so as to be seatable against the plunger when the cylinder is at its distal position.

21. An infusion system, of the type including a syringe with an axially-movable plunger, and a force-applying mechanism engageable against the plunger to apply an axially-directed actuation force thereto, characterized by the force-applying mechanism having a first position at which the magnitude of the total force applied to the plunger is at a maximum value but the axially-directed actuation force is less than the total force applied to the plunger, and a second position at which the magnitude of the total force applied to the plunger is less than its maximum value and the axially-directed actuation force is approximately equal to the total force applied to the plunger.

22. The system of claim 21, wherein the force-applying mechanism comprises:

a hollow cylinder in which the plunger is received;

a piston disposed for longitudinal movement within the cylinder between a proximal position and a distal position, the piston including a portion disposed so as to bear against the plunger;

a spring disposed within the cylinder and engaged with the piston so as to bias the piston toward its distal position, the spring being in a compressed state when the piston is at its proximal position, and in an extended state when the piston is at its distal position; and pivoting means, operative on the piston, for canting the piston with respect to the longitudinal axis when the piston is in its proximal position, and for causing the piston to pivot as it moves from its proximal position to its distal position under the force of the spring, until the piston is oriented substantially coaxially with the cylinder when the piston is at its distal position.

23. The device of claim 22, wherein the pivoting means comprises an inside diameter of the cylinder that gradually decreases from the proximal end of the cylinder to the distal end thereof.

24. The device of claim 23, wherein the piston comprises a hollow, substantially cylindrical portion having an open proximal end, a closed distal end bearing against the plunger, and an outside diameter that is slightly less than the minimum inside diameter of the cylinder.

25. The device of claim 24, wherein the distal end of the piston includes a proximal surface with an annular groove in which the spring is seated, the groove having a first circumferential position with a maximum depth, the groove progressively decreasing in depth toward a second circumferential position, diametrically opposite the first circumferential position, with a minimum depth.

26. The device of claim 24, wherein the closed distal end of the piston includes a distal surface having a distally-extending central protuberance seated against the plunger.

* * * * *

UNITED STATES PATENT AND TRADEMARK OFFICE
CERTIFICATE OF CORRECTION

PATENT NO.  : 5,599,315
DATED       : February 4, 1997
INVENTOR(S) : Charles J. McPhee.

It is certified that error appears in the above-indentified patent and that said Letters Patent is hereby corrected as shown below:

Title page, right column, item [73] Assignee, "Charles J. McPhee" should be -- I-Flow Corporation, Irvine, Calif. --.

Signed and Sealed this

Fifth Day of August, 1997

Attest:

BRUCE LEHMAN

*Attesting Officer*          *Commissioner of Patents and Trademarks*